United States Patent [19]
Holland

[11] Patent Number: 5,311,640
[45] Date of Patent: May 17, 1994

[54] DENTAL VACUUM APPARATUS

[76] Inventor: Robert S. Holland, P.O. Box 774, Georgetown, Conn. 06829

[21] Appl. No.: 934,020

[22] Filed: Aug. 21, 1992

[51] Int. Cl.⁵ ............................................. A47L 5/38
[52] U.S. Cl. ...................................... 15/353; 15/314; 15/413; 15/422.2; 417/423.8; 417/423.5
[58] Field of Search ............. 15/314, 353, 413, 422.2; 417/205, 423.5, 423.8

[56] References Cited

U.S. PATENT DOCUMENTS

| | | |
|---|---|---|
| Re. 24,755 | 12/1959 | Winter . |
| Re. 32,027 | 11/1985 | Hyatt et al. . |
| 184,461 | 11/1876 | Cooper . |
| 2,864,166 | 12/1958 | Shaw . |
| 3,012,322 | 12/1961 | Thompson . |
| 3,017,886 | 1/1962 | Thompson . |
| 3,078,579 | 2/1963 | Jones et al. . |
| 3,138,873 | 6/1964 | Bishop . |
| 3,240,000 | 3/1966 | Hayes et al. ............... 15/422.2 X |
| 3,291,508 | 12/1966 | Kolthoff, Jr. . |
| 3,457,645 | 7/1969 | Swanson . |
| 3,848,290 | 11/1974 | Bates ............... 15/422.2 X |
| 4,231,133 | 11/1980 | Probost . |
| 4,475,264 | 10/1984 | Schulz ............... 15/422.2 |
| 4,651,380 | 3/1987 | Ogden . |
| 4,783,878 | 11/1988 | McCambridge . |
| 4,934,017 | 6/1990 | Kent . |
| 5,099,543 | 3/1992 | Wade ............... 15/422.2 X |

FOREIGN PATENT DOCUMENTS 23036 7/1979 European Pat. Off. .

OTHER PUBLICATIONS

MVS Central Evacuation System (copyright 1972 by Densply International, Inc.) brochure.
AMETEK Lamb By-Pass Vacuum Motor Operating and Installation Instructions brochure.
Vortex Blowers In Series or Parallel (Spencer Turbine Company, Windsor Conn.) brochure.
AMETEK Bulletin WBM 570-0002 "Brushless DC Motor-Driven Blowers" brochure.

*Primary Examiner*—Chris K. Moore
*Attorney, Agent, or Firm*—Hayes & Reinsmith

[57] ABSTRACT

A dry vacuum apparatus for a dental operatory features an in-line configuration wherein a power unit subassembly is directly mounted upon a collection tank with a pair of brushless DC vacuum motor fan units in axially aligned, vertically stacked reverse relation with air inlets of the motors confronting one another and with a vacuum air outlet of one blower connected in series relation to a vacuum air inlet of the other blower, an air cooling circuit being provided for supplying cooling air to a common sealed plenum chamber servicing the confronting motor air inlets and also to the vacuum air inlets of the blowers.

22 Claims, 8 Drawing Sheets

DENTAL VACUUM APPARATUS

FIELD OF THE INVENTION

This invention generally relates to dental vacuum apparatus and particularly concerns so-called dry vacuum systems for servicing a dental operatory in the removal of solid matter, washings, and other waste mixtures resulting from dental procedures.

BACKGROUND OF THE INVENTION

Conventional dental vacuum systems require periodic, and frequently expensive, upkeep. Such upkeep may involve replacement and maintenance of motors required to produce the requisite vacuum for the dental operatories being serviced. Conventional wet system dental vacuums normally use a single large, powerful motor, or two such large motors mounted in parallel arrangements. When large motors of a turbine type are used, e.g., in parallel arrangements, such arrangements are normally for use in large dental offices and are quite expensive due primarily to the cost of such motors. In contrast, so-called dry systems typically generate vacuum with high speed vane type fans, and their operating motors are smaller and usually much noisier and shorter lived than conventional water sealed impeller type pumps used in wet systems. An air series arrangement in such dry systems, while known, is not widely adopted because an air exhaust from a first unit, e.g., serving to supply inlet air to a second unit causes that second unit to quickly heat up. This heat frequently results in premature motor failure within an unacceptably short period of time, particularly with small, inexpensive motors used for power operation of vacuum creating blowers.

OBJECTS OF THE INVENTION

A primary object of this invention is to provide a new and improved dry vacuum apparatus for a dental operatory and which is particularly designed to use relatively small, inexpensive vacuum motor fan units in a uniquely compact, aligned configuration with a collection tank.

Another object of this invention is to provide a new and improved dry vacuum apparatus of the type described wherein relatively small, inexpensive vacuum motor fan units are mounted in air series relation and provided with a simplified air cooling system for reliable, long term service under demanding conditions with minimized maintenance requirements.

Yet another object of this invention is to provide a new and improved dry vacuum apparatus of the type described which incorporates a flexible mounting coupling particularly suited to secure a pair of such vacuum motor fan units in aligned, stacked relation while additionally providing a common sealed plenum chamber for supplying cooling air to the motor inlets and a mechanically shock-free suspension without requiring conventional and typically high cost customized cabinetry.

A yet further object of this invention is to provide a new and improved dry vacuum apparatus incorporating a vacuum motor fan subassembly, as described, in an aligned configuration with a collection tank and which further provides a shutoff safety feature preventing damage to the overall system occurring from excessive water or foam accumulation within the tank.

Other objects will be in part obvious and in part pointed out in more detail hereinafter.

SUMMARY OF THE INVENTION

A dry vacuum apparatus of this invention features a pair of vacuum motor fan units each having a blower with a vacuum air inlet and a vacuum air outlet and a motor drivingly connected to that blower and having a motor cooling air inlet and a motor air outlet; mounting means form a common sealed plenum chamber and supports the vacuum motor fan units in axially aligned, stacked relation with their motor cooling air inlets adjacent one another and opening into the plenum chamber for communication with the motors; and an air cooling circuit includes an air supply line connected to the plenum chamber for supplying cooling air to the plenum chamber and to the motors.

A better understanding of the objects, advantages, features, properties and relations of the invention will be obtained from the following detailed description and accompanying drawings which set forth an illustrative embodiment and are indicative of the various ways in which the principle of the invention are employed.

DETAILED DESCRIPTION OF THE DRAWINGS

DESCRIPTION OF A PREFERRED EMBODIMENT

Figure 1:
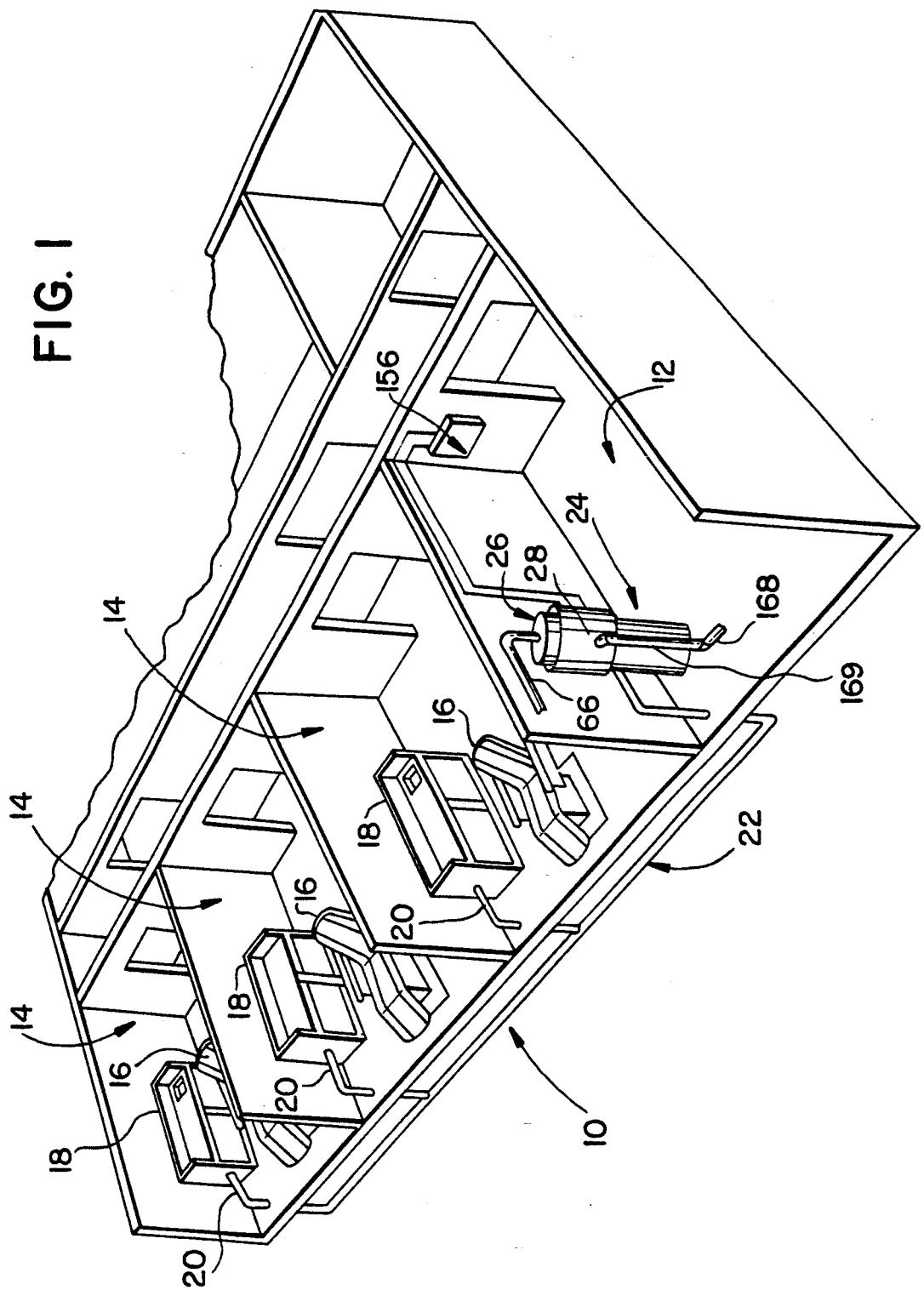
FIG. 1 is a perspective view, partly broken away, showing a dental office with a dental vacuum apparatus of this invention installed in a utility room.

Referring now in detail to the drawings, a dental office 10 is depicted in FIG. 1 showing a utility room 12 remote from operatories 14 of office 10. The operatories 14 each have dental chairs 16 and associated equipment 18 which will be understood to include such conventional dental items as cuspidors and evacuation hoses having intake nozzles, not shown, for use in evacuating body cavities such as in a mouth of a patient during surgery, e.g., to remove any resulting loose solids and liquid washings.

Figure 6:
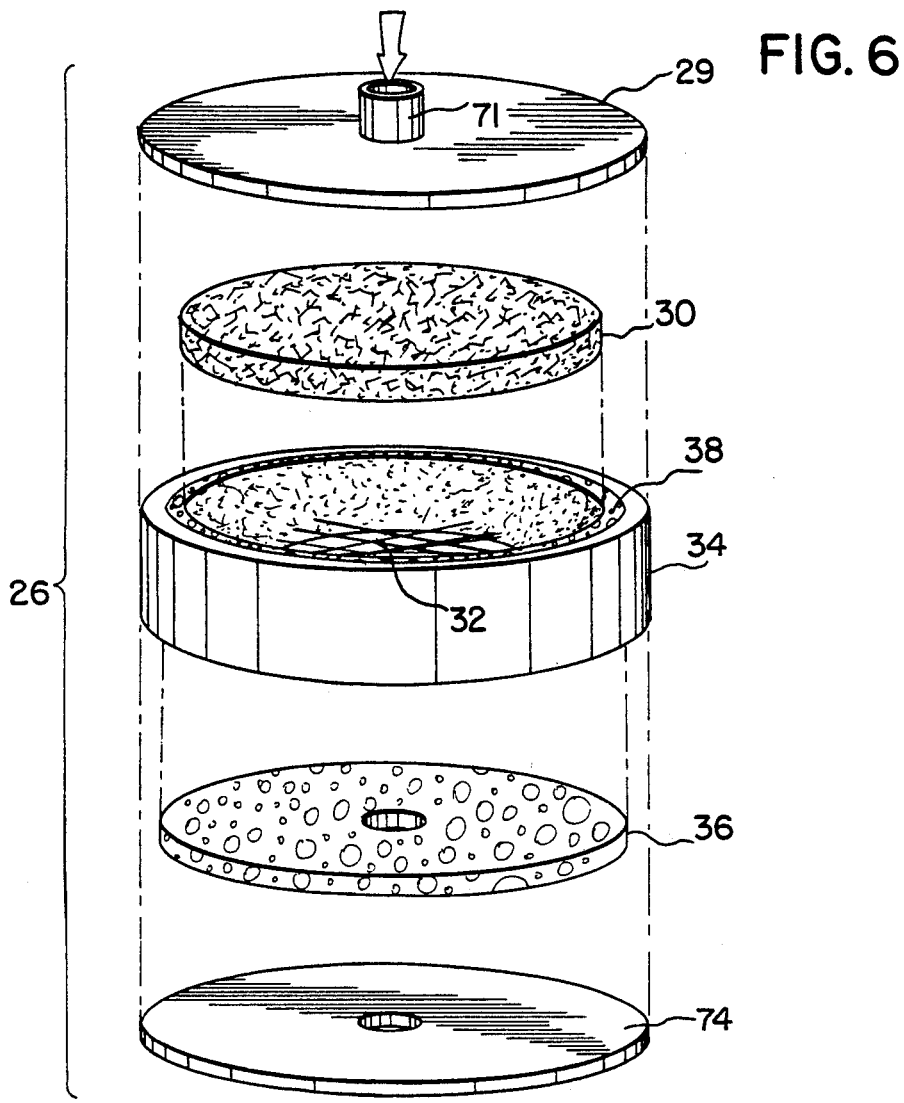
FIG. 6 is a perspective view showing components of a filter of the apparatus of this invention in disassembly.
Figure 7:
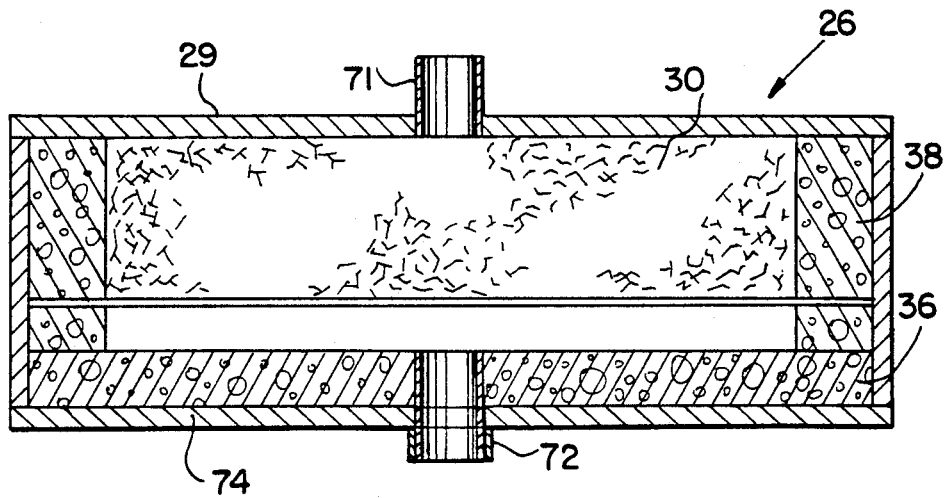
FIG. 7 is a side view, partly in section, of the filter of FIG. 6 in assembly.

To dispose of such waste mixtures, each operatory 14 is equipped with a vacuum line 20 connected to a common suction line 22 which in turn is connected to a central dental vacuum apparatus 24 installed in utility room 12. To ensure the longevity of the system, an air filter assembly 26 (FIGS. 6 and 7) is removably mounted on an upper shroud 28, for supplying cooling air to the apparatus 24 during operation as specifically described below. Air filter assembly 26 will be understood to have a removable cover 29 and filter 30. Filter 30 is made of any suitable loosely laid material which permits unimpeded air flow while entrapping undesired dust particles, the filter 30 being supported on cross wires 32 fixed within a filter canister 34. For sound-deadening, assembly 26 additionally has a bottom foam disc 36 which cooperates with an annular foam ring 38 surrounding the filter. Other suitable arrangements may be used, it being important only to supply clean cooling air.

Figure 4:
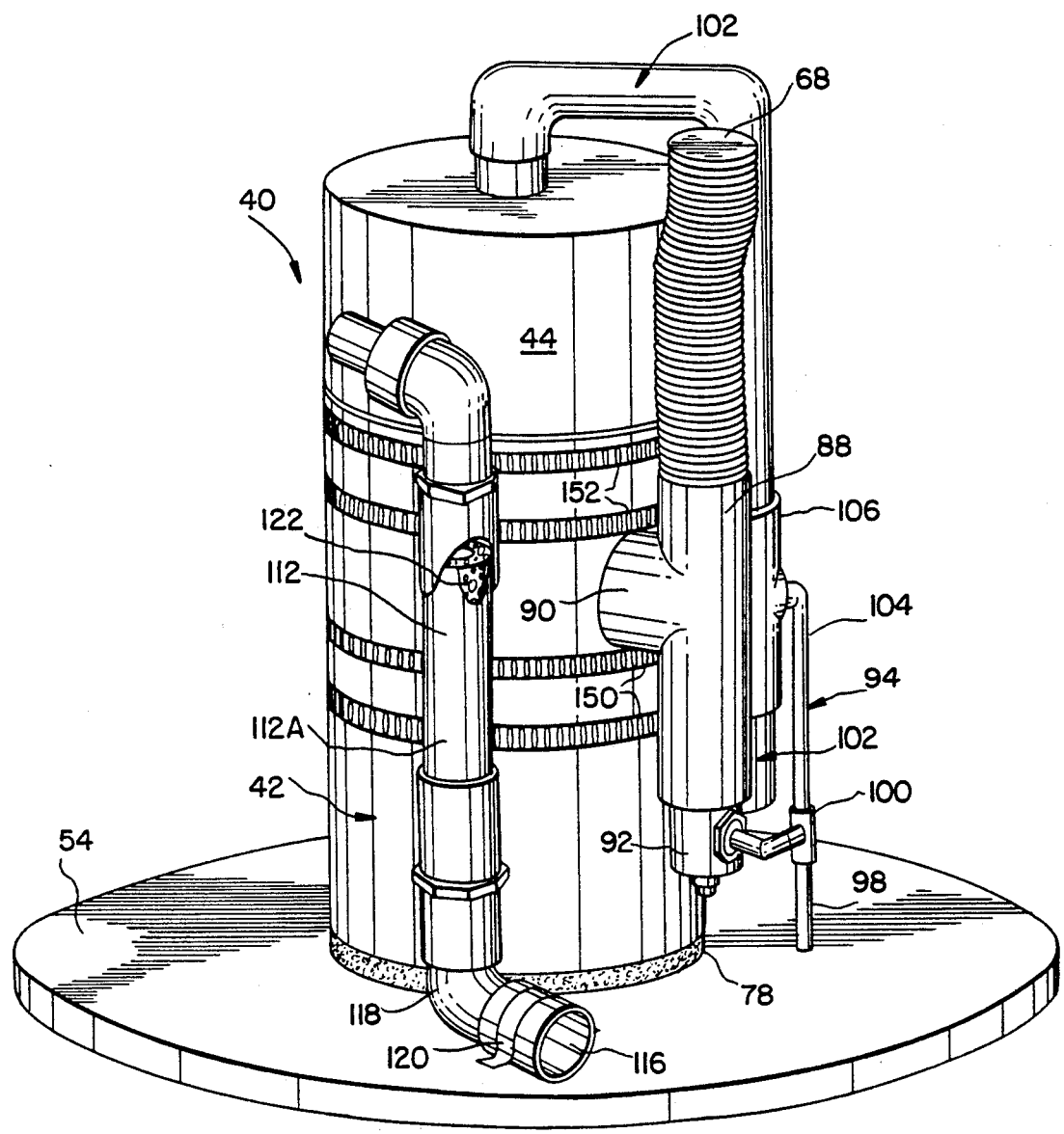
FIG. 4 is an enlarged perspective view of a power unit subassembly of the apparatus of this invention shown mounted on a collection tank cover.

To provide a compact apparatus requiring minimized plumbing connections and bends in a cost-effective structure, this invention contemplates using a power unit subassembly 40 (FIG. 4) comprising relatively small, low cost vacuum motor fan units 42, 44 (FIGS. 8 and 9) mounted in a unique arrangement to provide the requisite suction. More specifically, the power unit subassembly 40 includes a pair of such vacuum motor fan units 42, 44 each provided with a blower 46, 48 and an operating motor 50, 52 drivingly connected to blowers 46, 48 as best seen in FIG. 9. The subassembly 40 is supported on a removable cover 54 of an underlying cylindrical collection tank 56. Particularly efficient piping is achieved as fully described below by mounting the vacuum motor fan units 42, 44 in axially aligned, vertically stacked and reversed relation, with motor cooling air inlets 58, 60 of the motors 50, 52 confronting one another while ensuring that the requisite vacuum pulling power is provided by virtue of a vacuum air outlet 62 of a first blower 46 being connected to a vacuum air inlet 64 of the other blower 48 such that they operate in series relation.

To make such a series arrangement feasible when using inexpensive, relatively low capacity vacuum motor fan units, this invention further contemplates use of a simplified air cooling circuit to enable the smaller, less powerful motor-driven fan units to be used, as described above, in series. Specifically, cool outside air is fed to the units from any suitable source, e.g., from outside the utility room, through coolant air line 66 (FIG. 1), air filter assembly 26, and a main cooling air supply line or hose 68 (FIGS. 4, 8) connected to a plenum chamber 70 (FIG. 9) for supplying that cooling air to the plenum chamber 70 and to the motors 50, 52. Air line 66 connects to intake fitting 71 on filter cover 29. Main air supply hose 68 connects through an intake air fitting 72 (FIG. 7) on base 74 of the filter assembly 26 to extend downwardly within upper shroud 28 which surrounds power unit subassembly 40 shown supported on a resilient pad 78 sandwiched between the base of the lower or first blower 46 and cover 54 for damping undesired motor vibration and providing a vacuum seal.

Figure 2:
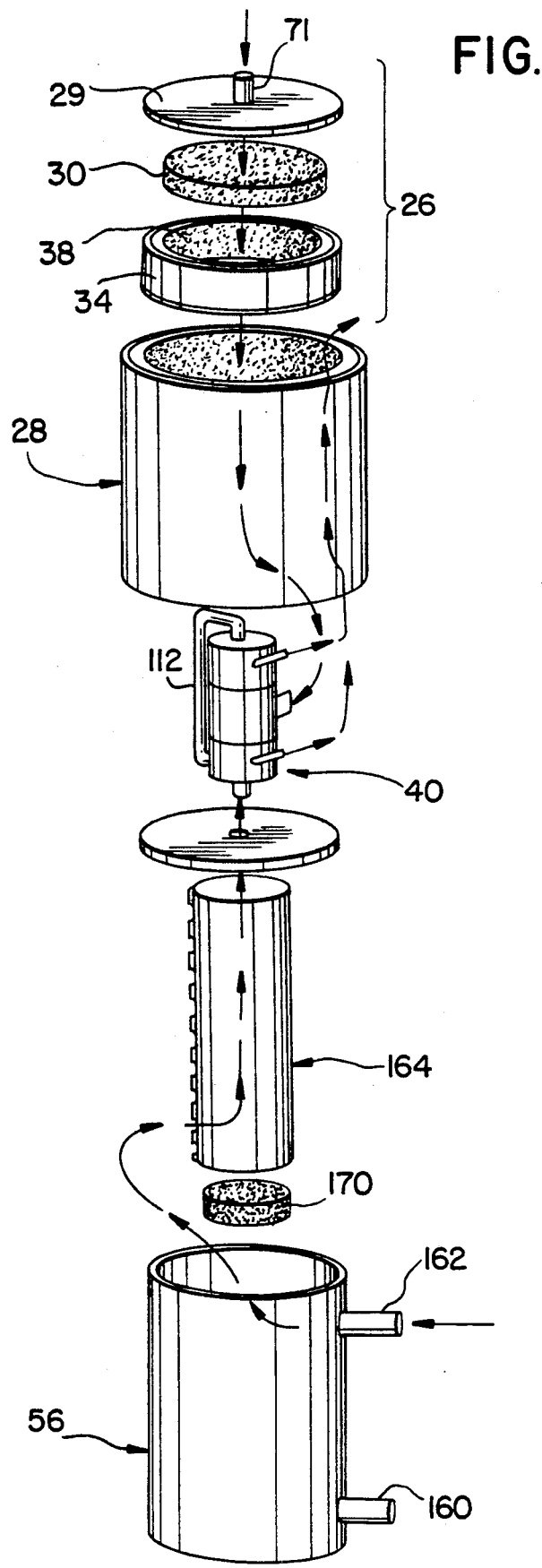
FIG. 2 is an exploded view showing certain components of the apparatus of FIG. 1.
Figure 3:
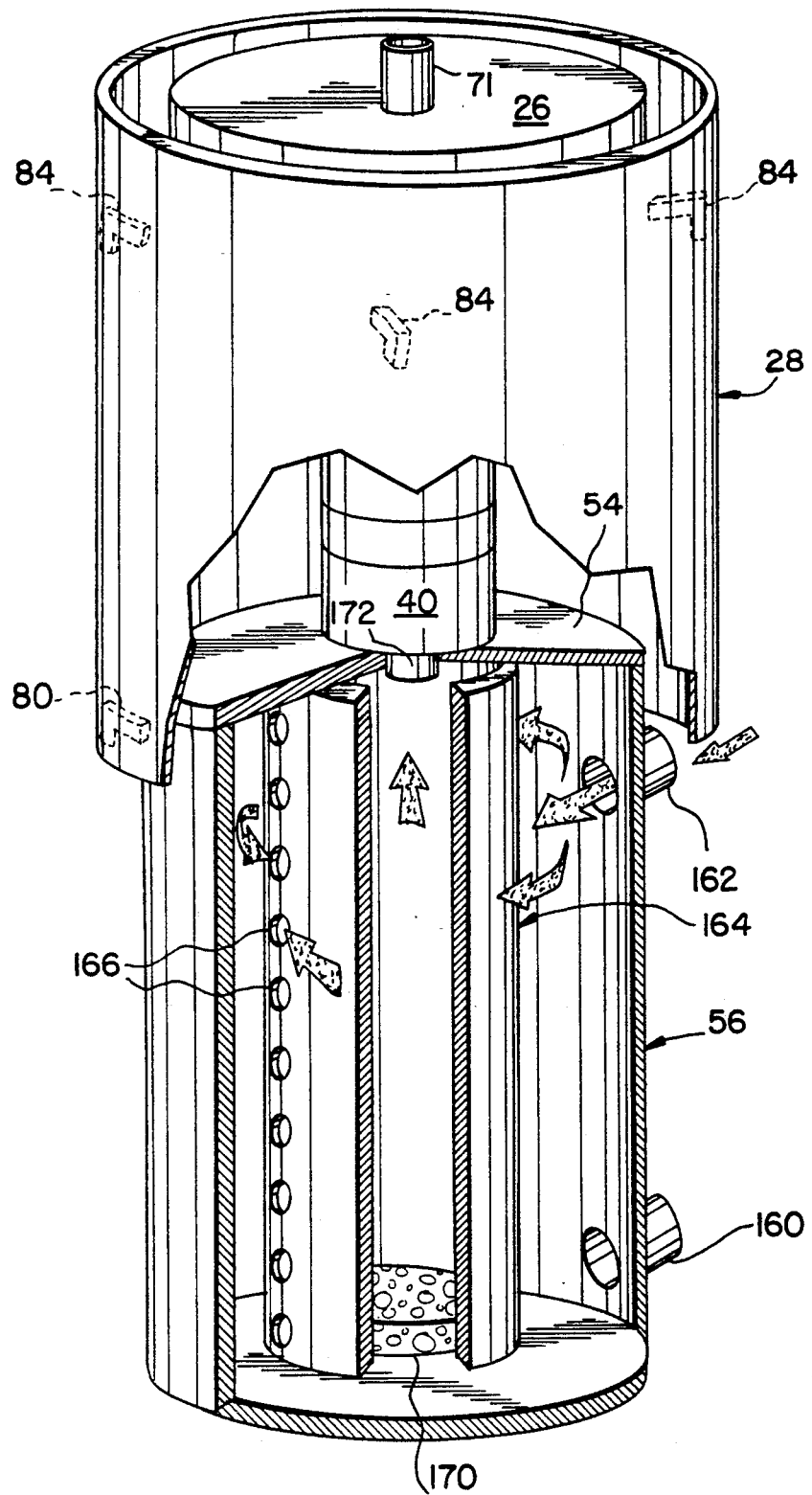
FIG. 3 is an enlarged perspective view, partly in section and partly broken away, showing the dental vacuum apparatus of this invention with certain parts removed for clarity.
Figure 5:
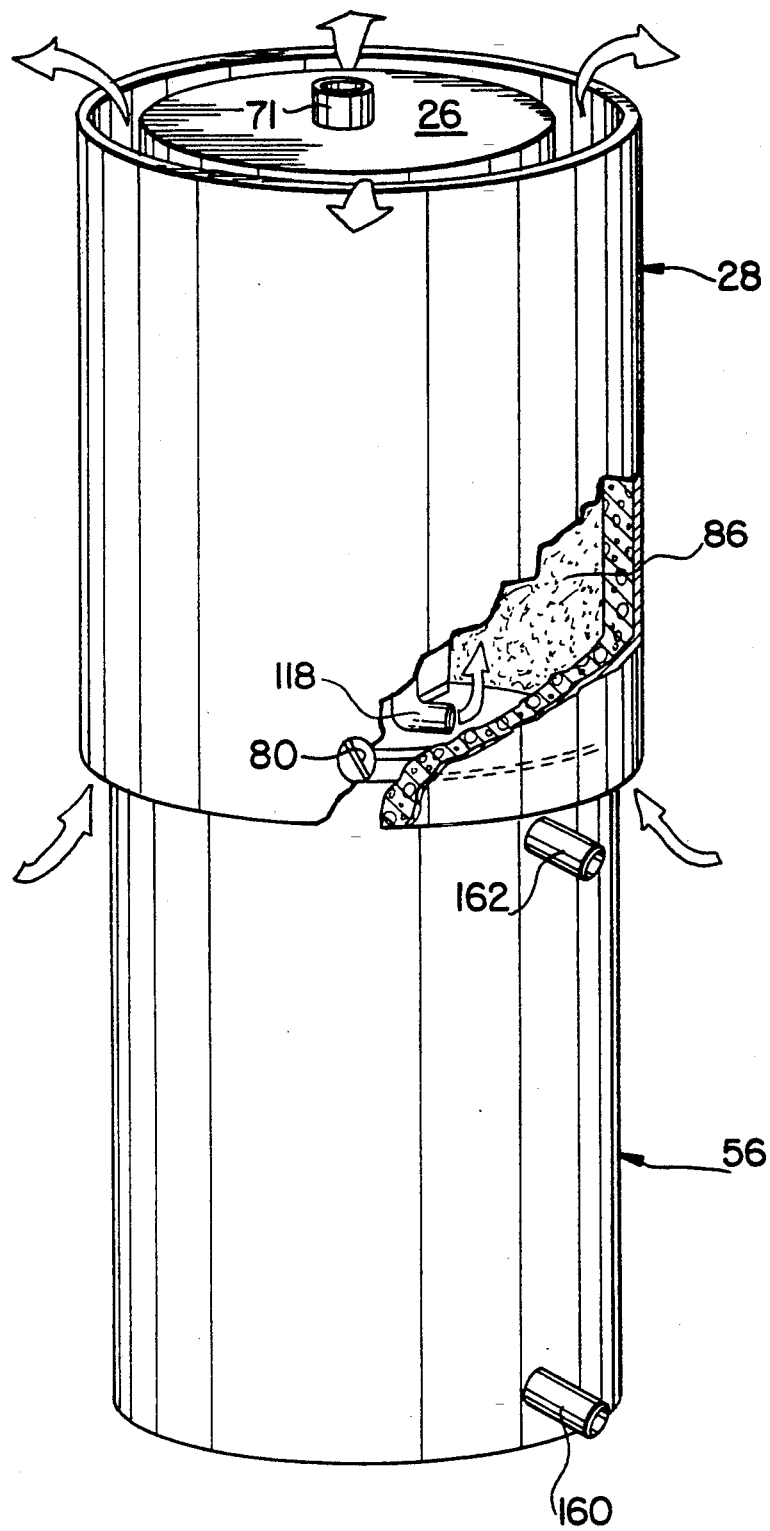
FIG. 5 is a view similar to FIG. 3 showing ambient air flow created by the power unit subassembly of FIG. 4.

In the specifically illustrated embodiment, upper shroud 28 is shown having a series of four lower stand-off supports at 80 equally spaced apart and contained in a common plane. These supports are shown in the form of L shaped brackets (FIG. 9) attached to shroud 28. Upon engagement of stand-off supports 80 with the upper surface of cover 54, shroud 28 is disposed in outwardly radially spaced relation to collection tank 56 defining an annular opening 82 at the base of shroud 28. Free entry of ambient air is thus permitted into the space within the shroud 28 above tank 56 wherein power unit subassembly 40 is housed, it being understood that the minimum diameter of upper shroud 28 is greater than the maximum diameter of the underlying collection tank 56 and its cover 54. A corresponding series of stand-off supports shown at 84 are mounted adjacent an upper end of upper shroud 28 for supporting air filter assembly 26 in spaced relation to shroud 28, thus ensuring free flow of air (FIGS. 2, 5) into the shroud 28 through annular opening 82 and out through its upper end to prevent the space within the shroud from becoming warmer than the ambient air within utility room 12. To provide further sound silencing, a foam insulator sleeve 86 fits inside upper shroud 28 between the upper and lower series of stand-off supports 80, 84.

In the specifically illustrated embodiment, air supply hose 68 connects to a main air supply pipe 88 (FIGS. 8 and 9) having an intermediate laterally projecting conduit 90 opening into plenum chamber 70 between the two vacuum motor fan units 42, 44. A downstream end of pipe 88 connects through a vacuum relief valve 92 to an auxiliary conduit 94 which directs cooling air to vacuum air inlets 96, 64 of blowers 46, 48 in an air parallel arrangement.

Should operatories 14 be switched off while power unit sub-assembly 40 remains in operation, tank 56 essentially is sealed, the only incoming air to tank 56 being from restricted intake nozzles within the operatories 14. To maintain continuous cooling of the activated power unit subassembly 40, particularly when vacuum lines 20 are not actively pulling vacuum, air is continuously supplied in accordance with this invention to that power unit subassembly 40.

While different approaches may be used to provide that cooling air, this preferred embodiment (FIG. 9) shows an auxiliary cooling air supply line which extends downwardly from a T-fitting 100 of auxiliary conduit 94 through an opening in cover 54 to supply cooling air which may then be drawn from tank 56 upwardly into vacuum air inlet 96 of blower 46. The air cooling circuit further includes a blower interconnecting conduit 102 extending between vacuum air outlet 62 of the first blower 46 and vacuum air inlet 64 of second blower 48. Auxiliary conduit 94 also has a run 104 extending upwardly from fitting 100 into another T-fitting 106, thus connecting auxiliary conduit 94 and blower interconnecting conduit 102 for supplying cooling air to vacuum air inlet 64 of second blower 48 wherein that cooling air is mixed with and cools vacuum air discharged from first blower 46. It will be understood that auxiliary air supply line 98 is intentionally of restricted size, say, 5/64 inch inside diameter, relative to the auxiliary conduit run 104, e.g., having a ½ inch inside diameter, because the first blower 46 otherwise would normally draw significantly higher volume of coolant air than that drawn by blower 48. By virtue of the disclosed arrangement, blower 48 serves to effectively draw a vacuum through the blower interconnecting conduit 102 and assist the flow of cooling air from auxiliary conduit run 104 to blower 48.

Vacuum relief valve 92 is normally wide open at the time the system is initially activated. As each operatory 14 in office 10 is brought into operation, suction in main air supply hose 68 decreases. A reset spring, not shown, will be understood to be mounted within vacuum relief valve 92 which spring acts to gradually close down and reduce cooling air flow through auxiliary conduit 94 to blowers 46, 48. Auxiliary air supply line 98 supplies a constant flow of cooling air under relatively steady pressure to vacuum air inlet 96 of first blower 46, but that air flow is reduced in the volume permitted to pass through because of the restricted size of auxiliary air supply line 98.

To discharge air from blower chambers 108, 110 to atmosphere, a vacuum exhaust line 112 is connected to vacuum air outlet 114 of second blower 48. As best seen in FIG. 9, vacuum exhaust line 112 extends from an upper U-shaped end through a depending run 112A alongside power unit subassembly 40 to terminate at an outlet 116 of an elbow 118 extending through a clamp 120 on cover 54. To minimize undesired noise, depending run 112A is preferably fitted with a muffler such as internal insulating sleeve shown at 122.

In addition to air exhaust from blowers 46, 48 being discharged into the confines of upper shroud 28, motors 50, 52 include internal ventilating fans 124, 126 supported on drive shafts 128, 130 for passing air through their motor chambers 132, 134 before discharging through motor air outlets 136, 138 formed in side walls of their respective housings 146, 148. Air flow from motor chambers 132, 134 exits in a radial direction relative to major axes 140, 142 of the housings 146, 148. These motor air outlets 136, 138 are shown (FIG. 9) as exhaust ports communicating motor chambers 132, 134 of each vacuum motor fan unit 42, 44 with the surrounding space formed within upper shroud 28. As shown, motor chamber 132, 134 and blower chambers 108, 110 are isolated relative to one another within their respective housings.

A power unit subassembly 40 of the above described construction has been found to operate satisfactorily using AMETEK "Windjammer" DC brushless DC motor-driven blowers identified as Model No. 116632-01 which operate on 120 volt AC (50/60 HZ, 4.5 amps) and are manufactured by Lamb Electric Division, Kent, Ohio. It is also contemplated to use such DC brushless motors which operate on 230 volt alternating current. Albeit these are relatively small and inexpensive vacuum motor fan units, by providing an air cooling system with parallel connections for supplying cooling air to the blowers and running the blowers as described above in series, it has been found that vacuum of about 7 inches mercury is pulled while using the disclosed air cooling circuit to provide adequate volume of air flow to prevent overheating of second blower 48 so as to extend the bearing life of power unit subassembly 40. Blower 46 also is protected against overheating by the described air cooling supply line 98 should the operatories 14 be shut off without deactivating the power unit subassembly 40. Thus a relatively powerful, compact power unit is provided to pull solid and liquid waste mixtures as required while yet being particularly cost effective because of the nature of the motors being used and the simplified plumbing featured by this disclosed design. In addition, problems commonly encountered in conventional dental vacuums due to brush failure are eliminated.

For directing clean cooling air into motor chambers 132, 134 for high efficiency heat transfer while simultaneously preventing entry of warm ambient air of utility room 14 being drawn into the motor chambers, a sealed plenum chamber 70 is formed between the vertically stacked, axially aligned vacuum motor fan units 42, 44 in a mechanically shock-free mounting without requiring conventional high cost customized casings or cabinetry. Specifically, a resilient, elastomeric sleeve 144 is shown formed to extend about end portions of housings 146, 148 of the vacuum motor fan units 42, 44 in hermetically tight engagement with their sidewalls to define sealed plenum chamber 70 communicating with main air supply pipe 88 through its conduit 90 and with motor air inlets 58, 60 serving motors 50, 52.

Figure 8:
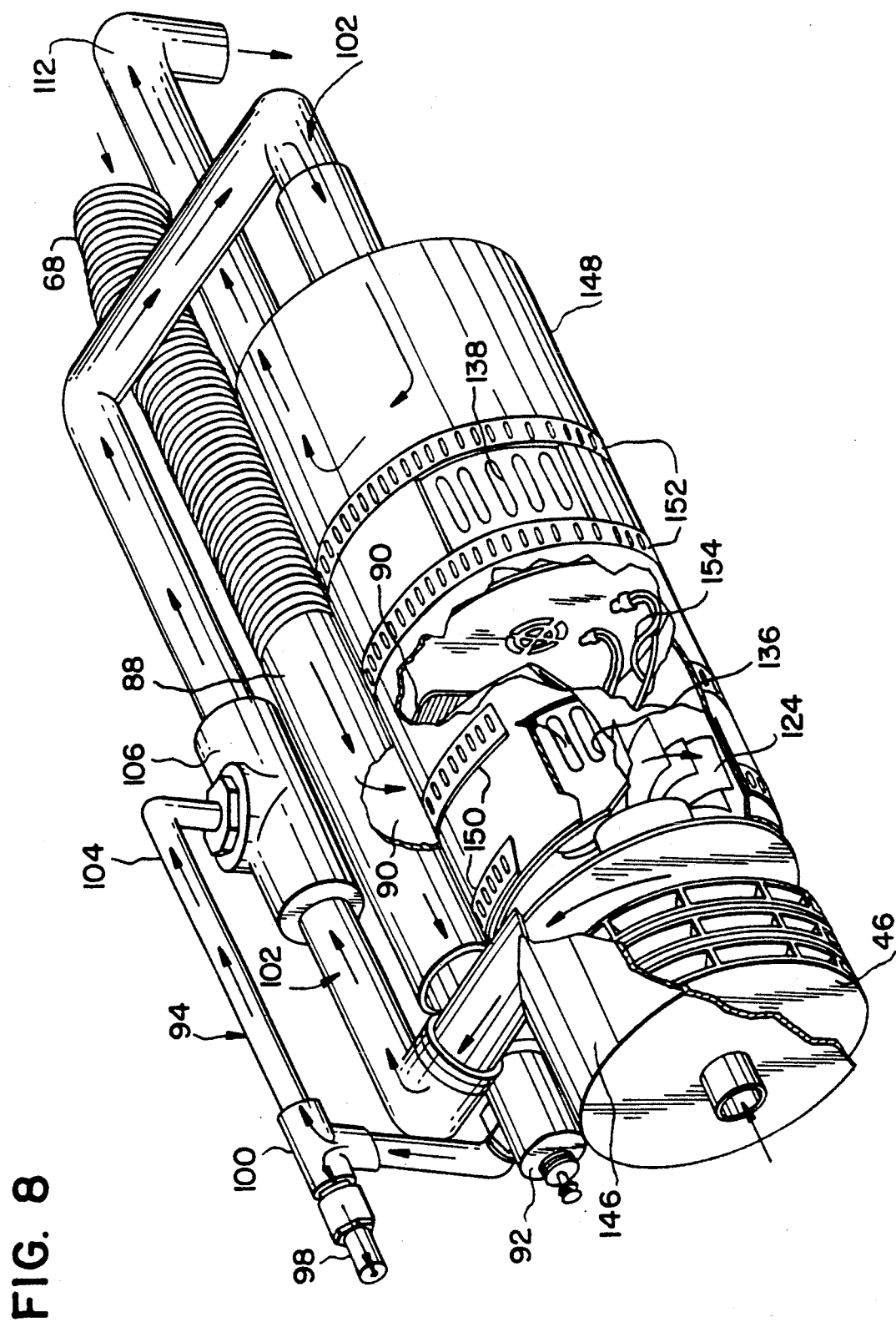
FIG. 8 is a perspective view, partly broken away and partly in section, of the power unit subassembly of FIG. 4.
Figure 9:
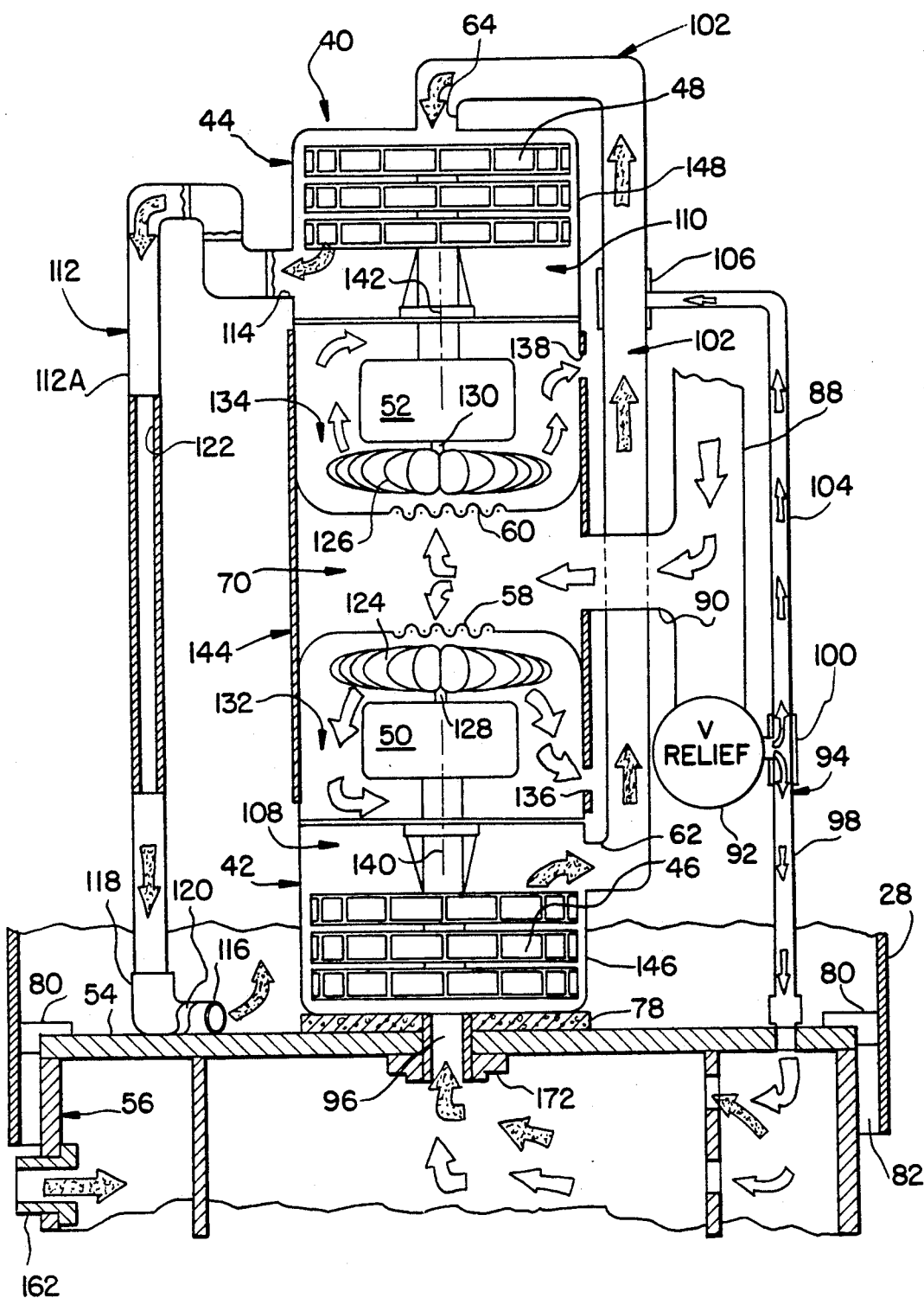
FIG. 9 is a schematic view of the air flow patterns of the power unit subassembly of FIG. 4.

In the specific embodiment, sleeve 144 is shown secured to housings 146, 148 by worm screw hose clamps 150, 152 (FIG. 8). A pair of such clamps are shown spaced apart and extending about each end of sleeve 144 with exhaust ports provided between each pair of clamps by cut-out openings in sleeve 144 which register with motor air outlets 136, 138 formed in the housing sidewall of each motor 50, 52. The simplicity and resiliency of such a coupling accommodates stresses imposed by starting torque, as well as high vacuum levels which may be encountered during operation of the apparatus 24. In addition, the described mounting coupling also serves as a convenient junction box for receiving wiring such as at 154 from a power supply such as electrical panel 156 (FIG. 1) to the motors 50, 52.

During operation of apparatus 24 and upon its being activated, tank 56 is under vacuum, and a check valve, not shown, in discharge outlet 160 at the bottom of tank 56 is closed to prevent discharge. Tank 56 then is subjected to a high volume of air flow through main suction line 22 which enters tank 56 through upper fitting 162 in a highly turbulent state. To reduce incoming air flow velocity and prevent undesired turbulence within tank 56, a baffle 164 of a cylindrical configuration is installed within tank 56 to disperse that air flow. To permit entry of air into overlying vacuum air inlet 96 to first blower 46 without entraining waste particles from the incoming air flow to tank 56, a series of vertically aligned ports 166 extend longitudinally along baffle 164 in diametrically opposed relation to main suction line fitting 162 on tank 56.

The collection tank 56 and its baffle 164 are preferably sized to accommodate waste and debris collected in a day's time from all operatories being served. Upon switching off the power in each operatory 14 and deactivating the system, vacuum is lost in tank 56 and a check valve, not shown, in outlet 160 opens automatically to permit drainage through pipe 168 (FIG. 1) of the accumulated waste from tank 56. To minimize ambient temperature in utility room 12, the exhaust outlet 116 of line 112 may, if desired, by connected via line 169 to pipe 168 to exhaust into drainage pipe 168 downstream of any check valve in that pipe.

To provide a safety feature responsive to deactivate the system upon the liquid level in tank 56 reaching a predetermined level, a float, e.g., in the form of a foam disc 170 is installed within the baffle 164. As liquid collects, float 170 rises and deactivates the system by blocking intake fitting 172 (FIG. 9) leading to vacuum air inlet 96 of first blower 46. Should a foaming agent be accidentally discharged into one of the vacuum lines 20 leading to the main suction line 22, foam may rise through the height of baffle 164 within seconds. Float 170, however, will automatically rise with the foam, and the upper surface of float 170 will automatically close off intake fitting 172 and prevent any foam or water from causing damage, particularly to vacuum motor fan units using semi-sealed bearings.

By virtue of the above described construction, a dry dental vacuum apparatus is disclosed which provides two essential air flow patterns, one for cooling air and the other for warm ambient working air. These air flow patterns are particularly designed to permit use of the disclosed low-cost, relatively small, DC brushless vacuum motor fan units in series relation to provide reliable performance over extended periods of time under demanding conditions without undesired failures. The simplicity and relatively low cost of the apparatus is significantly enhanced by the disclosed mounting coupling for supporting the vacuum motor fan units in axially aligned, reversed relation with the motor air inlets confronting one another. In addition, the simplified baffle/float arrangement disclosed is particularly useful as a safety feature with the disclosed in-line installation of the collection tank/power unit subassembly to prevent accidental damage to the apparatus.

As will be apparent to persons skilled in the art, various modifications, adaptations and variations of the foregoing specific disclosure can be made without departing from the teachings of this invention.

I claim:

1. A vacuum apparatus for a dental operatory comprising
    (a) a pair of vacuum motor fan units, each unit including
        (i) a blower with a vacuum air inlet and a vacuum air outlet, and
        (ii) a motor drivingly connected to the blower and having a motor air inlet and a motor air outlet,
        (iii) the vacuum air outlet of one of the pair of blowers being connected in series relation to the vacuum air inlet of the other blower,
    (b) mounting means forming a common sealed plenum chamber and maintaining the vacuum motor fan units with their motor air inlets adjacent one another and opening into the plenum chamber for communicating the plenum chamber with the motors, and
    (c) an air cooling circuit including and air supply line connected to the plenum chamber for supplying cooling air to the plenum chamber and to the motors.

2. The apparatus of claim 1 wherein the air cooling circuit includes an auxiliary conduit means for directing cooling air to the vacuum air inlet of each of the pair of blowers.

3. The apparatus of claim 1 wherein the vacuum motor fan units each includes a housing with the blower and motor coaxially mounted therein relative to a major axis of the housing, the vacuum motor fan units being maintained by the mounting means in axially aligned, reversed stacked relation with their motor air inlets confronting one another.

4. The apparatus of claim 3 wherein the mounting means comprises an elastomeric sleeve extending about end portions of the housings of the vacuum motor fan units in sealed engagement therewith such that said plenum chamber is sealed and is solely communicating with the air supply line and the motor air inlets of the vacuum motor fan units.

5. The apparatus of claim 3 wherein the motors each include an internal ventilating fan, wherein the vacuum air inlets of the blowers and the motor air inlets of the motors are in axial alignment, and wherein the vacuum air outlets of the blowers and the motor air outlets of the motors are formed in sidewalls of their respective housings for discharging air from the blowers and from the motors radially relative to the major axes of the housings.

6. The apparatus of claim 1 wherein each of the vacuum motor fan units includes a housing having a motor chamber, a blower chamber and sealing means isolating the motor chamber and blower chamber from one another, each motor having a ventilating fan mounted within its motor chamber for drawing cooling air therein from the plenum chamber through the motor air inlet.

7. The apparatus of claim 6 wherein a vacuum exhaust line is connected to the vacuum air outlet of said other blower for discharging air exhausted from the blower chambers to atmosphere.

8. The apparatus of claim 1 wherein the motor of each unit is a DC brushless motor designed to operate on alternating current.

9. The apparatus of claim 1 wherein a tank is provided for collecting waste mixtures from a dental operatory, and wherein the vacuum motor fan units are vertically stacked in overlying relation to the tank with the vacuum air inlet of said one blower in communication therewith.

10. The apparatus of claim 9 wherein the tank includes a suction line intake and a generally cylindrical baffle mounted within the tank in confronting relation to the suction line intake for minimizing turbulence of incoming air therethrough, the baffle including ports therein on a side of the baffle opposite the suction line intake, and a float received within the baffle for closing off the vacuum air inlet of said one blower upon the float rising to a predetermined height in the baffle within the tank.

11. A vacuum apparatus for a dental operatory comprising
    (a) a pair of vacuum motor fan units, each unit including
        (i) a housing,
        (ii) a blower with a vacuum air inlet and a vacuum air outlet, and
        (iii) a motor drivingly connected to the blower and having a motor air inlet and a motor air outlet,
    (b) a resilient sleeve engaging end portions of the housing and maintaining the vacuum motor fan units in axially aligned, reversed tandem relation with their motor air inlets confronting one another, the sleeve forming a common sealed plenum chamber in communication with the motors,
    (c) an air cooling circuit including
        (i) an air supply line connected to the plenum chamber for supplying cooling air to the plenum chamber and to the motors, and
        (ii) an auxiliary air supply conduit in communication with the air supply line and connected in parallel to the vacuum air inlets of the blowers, and
    (d) a blower interconnecting conduit connecting the vacuum air outlet of one blower and the vacuum air inlet of the other blower in series relation.

12. The apparatus of claim 11 wherein the vacuum air inlets of the blowers and the motor air inlets of the motors are in axial alignment, and wherein the vacuum air outlets of the blowers and the motor air outlets of the motors are formed in sidewalls of their respective housings for radially discharging air from the blowers and from the motors.

13. The apparatus of claim 11 wherein the housing of each of the vacuum motor fan units includes a motor chamber and a blower chamber in isolated relation from one another, each motor having a ventilating fan mounted within its motor chamber for drawing cooling air therein from the plenum chamber through the motor air inlet.

14. The apparatus of claim 11 wherein a vacuum exhaust line is connected to the vacuum air outlet of said other blower for discharging air exhausted from the blowers to atmosphere, and wherein the auxiliary air supply conduit includes first and second air supply lines respectively connected to vacuum air inlets of said one blower and said other blower, the first air supply line being of restricted size relative to the second air supply line.

15. The apparatus of claim 11 further including a tank for collecting dental operatory waste mixtures, wherein the vacuum motor fan units are vertically stacked on the tank with the vacuum air inlet of said one blower in communication therewith.

16. The apparatus of claim 15 wherein the tank includes a suction line intake and a generally cylindrical baffle mounted within the tank in confronting relation to the suction line intake for minimizing turbulence of incoming air therethrough, the baffle including ports therein on a side of the baffle opposite the suction line intake, and a float received within the baffle for closing off the vacuum air inlet of said one blower upon the float rising to a predetermined height in the baffle within the tank.

17. The apparatus of claim 11 wherein a vacuum relief valve is mounted in the auxiliary air supply conduit.

18. A dry vacuum apparatus for a dental operatory comprising
 (a) a vacuum power unit including a pair of motor-driven blowers each including a vacuum air inlet and a vacuum air outlet,
 (b) a resilient sleeve maintaining the motor-driven blowers in aligned, tandem relation and forming a common sealed plenum chamber for supplying motor air,
 (c) a tank for collecting dental operatory waste mixtures, the power unit being supported by the tank with a vacuum air inlet of one of the blowers in communication with the tank,
 (d) an air cooling circuit including
  (i) an air supply line connected to the plenum chamber for supplying motor cooling air from an outside source to the plenum chamber, and
  (ii) an auxiliary air supply conduit in communication with the air supply line and connected in parallel to the vacuum air inlets of the blowers, and
 (e) a blower interconnecting conduit connecting the vacuum air outlet of said one blower in series with the vacuum air inlet of the other blower.

19. The apparatus of claim 18 wherein a vacuum exhaust line is connected to the vacuum air outlet of said other blower for discharging air exhausted from the blowers to atmosphere.

20. The apparatus of claim 18 wherein each unit includes a DC brushless motor designed to operate on alternating current, the motor being drivingly connected to the blower and having a motor inlet and a motor outlet, the sleeve supporting the motor-driven blowers in reversed stacked relation with their motor air inlets confronting one another and opening into the common sealed plenum chamber.

21. The apparatus of claim 18 wherein the auxiliary air supply conduit includes first and second air supply lines respectively connected to vacuum air inlets of said one blower and said other blower, the first air supply line being of restricted size relative to the second air supply line.

22. The apparatus of claim 18 wherein the tank includes a suction line intake and a generally cylindrical baffle mounted within the tank in confronting relation to the suction line intake for minimizing turbulence of incoming air therethrough, the baffle including ports therein on a side of the baffle opposite the suction line intake, and a float received within the baffle for closing off the vacuum air inlet of said one blower upon the float rising to a predetermined height in the baffle within the tank.

* * * * *